(12) United States Patent
Kim et al.

(10) Patent No.: US 11,213,572 B2
(45) Date of Patent: Jan. 4, 2022

(54) CARTILAGE REGENERATION COMPOSITION CONTAINING HAPLN1 AS ACTIVE INGREDIENT

(71) Applicant: HAPLNSCIENCE INC., Gyeonggi-do (KR)

(72) Inventors: Dae Kyong Kim, Gyeonggi-do (KR); Ji Min Jang, Seoul (KR)

(73) Assignee: HAPLNSCIENCE INC., Gyeonggi-do (KR)

( * ) Notice: Subject to any disclaimer, the term of this patent is extended or adjusted under 35 U.S.C. 154(b) by 0 days.

(21) Appl. No.: 16/805,420

(22) Filed: Feb. 28, 2020

(65) Prior Publication Data

US 2020/0276278 A1  Sep. 3, 2020

Related U.S. Application Data

(63) Continuation of application No. PCT/KR2018/009996, filed on Aug. 29, 2018.

(30) Foreign Application Priority Data

Aug. 29, 2017 (KR) .................. 10-2017-0109422
Aug. 23, 2018 (KR) .................. 10-2018-0098497

(51) Int. Cl.
| | |
|---|---|
| A61K 38/39 | (2006.01) |
| A61K 9/00 | (2006.01) |
| A61P 19/00 | (2006.01) |
| A61P 19/04 | (2006.01) |
| A23L 33/10 | (2016.01) |
| A61K 31/728 | (2006.01) |

(52) U.S. Cl.
CPC ............ *A61K 38/39* (2013.01); *A61K 9/0056* (2013.01); *A61K 31/728* (2013.01); *A61P 19/04* (2018.01)

(58) Field of Classification Search
CPC .............. A61K 31/728; A61K 2300/00; A61K 38/1709; A61K 38/39; A61K 9/0056; A23L 33/10; A61P 19/00; A61P 19/04
See application file for complete search history.

(56) References Cited

U.S. PATENT DOCUMENTS

| | | | |
|---|---|---|---|
| 2008/0139500 A1* | 6/2008 | Goldberg | A61P 19/02 514/54 |
| 2012/0171171 A1 | 7/2012 | West et al. | |
| 2013/0052198 A1* | 2/2013 | Milwid | A61P 1/04 424/137.1 |
| 2014/0178988 A1 | 6/2014 | West et al. | |
| 2016/0220699 A1 | 8/2016 | O'Heeron | |

FOREIGN PATENT DOCUMENTS

| | | |
|---|---|---|
| JP | 5767591 B2 | 8/2015 |
| JP | 2016-531147 | 10/2016 |
| KR | 10-2017-0031060 A | 3/2017 |
| KR | 10-2019-0024727 | 3/2019 |
| WO | 2014-130411 A1 | 8/2014 |
| WO | 2017-123951 A1 | 7/2017 |

OTHER PUBLICATIONS

Urano et al, "Single-nucleotide polymorphism in the hyaluronan and proteoglycan link protein 1 (HAPLN1) gene is associated with spinal osteophyte formation and sick degeneration in Japanese women," Eur Spine J, 2011, 20: 572-577. (Year: 2011).*
Czipri, et al., Genetic Rescue of Chondrodysplasia and the Perinatal Lethal Effect of Cartilage Link Protein Deficiency, The Journal of Biological Chemistry, Oct. 3, 2003, pp. 39214-39223, vol. 278 (40).
Tomohiko Urano, et al., *Single-nucleotide polymorphism in the hyaluronan and proteoglycan link protein 1 (HAPLN1) gene is associated with spinal osteophyte formation and disc degeneration in Japanese women*, published Oct. 15, 2010, 6 pages.
Tiffany Cheng, et al., *Comparison of Gene Expression Patterns in Articular Cartilage and Dedifferentiated Articular Chondrocytes*, published Aug. 1, 2011, 12 pages.
International Search Report and Written Opinion for PCT/KR2018/009996, dated Dec. 17, 2018, 14 pages.
Blaney Davidson et al., "Reduced transforming growth factor-beta signaling in cartilage of old mice: role in impaired repair capacity," Arthritis Research & Therapy, 7:R1338-R1347, 2005.
Extended European Search Report dated Mar. 30, 2021 for European Patent Application No. 18851068.9 (9 pages).
Notice of Reasons for Refusal dated Mar. 1, 2021 for Japanese Patent Application No. 2020-512483 (6 pages; English translation attached).
Tekari et al., "Transforming Growth Factor Beta Signaling Is Essential for the Autonomous Formation of Cartilage-Like Tissue by Expanded Chondrocytes," PLoS One, 10(3):e0120857 (17 pages), 2015.
Wang et al., "TGFβ Signaling in Cartilage Development and Maintenance," Birth Defects Res C Embryo Today, 102(1):37-51, 2014 (Author Manuscript version, 25 pages).

* cited by examiner

*Primary Examiner* — Julie Ha
(74) *Attorney, Agent, or Firm* — Klarquist Sparkman, LLP (57) ABSTRACT

Provided is a method of regenerating cartilage tissues by treatment with hyaluronan and proteoglycan link protein 1 (HAPLN1), and a composition for regenerating cartilage, the composition including HAPLN1 as an active ingredient. According to the present disclosure, the HAPLN1 protein may have cartilage formation-stimulating ability and articular cartilage regeneration ability, may increase an expression level of TGF-β receptor I of chondrocytes to increase a component ratio of cells having cartilage formation ability, and to induce regeneration of cartilage tissues. Accordingly, the HAPLN1 protein of the present disclosure, which is a novel composition regulating TGF-β signaling, may be usefully applied as a pharmaceutical composition for regenerating cartilage, a health food composition for regenerating cartilage, or a reagent composition for regenerating cartilage.

6 Claims, 4 Drawing Sheets

Specification includes a Sequence Listing.

CARTILAGE REGENERATION COMPOSITION CONTAINING HAPLN1 AS ACTIVE INGREDIENT

RELATED APPLICATIONS

The present application is a continuation of PCT Application No. PCT/KR2018/009996 filed Aug. 29, 2018, which claims priority to Korean Patent Applications No. 10-2017-0109422, filed Aug. 29, 2017, and No. 10-2018-0098497, filed Aug. 23, 2018, all of which are hereby incorporated in their entirety by reference as set forth herein.

TECHNICAL FIELD

The present disclosure relates to a method of regenerating cartilage tissues by treatment with hyaluronan and proteoglycan link protein 1 (HAPLN1) and a composition for regenerating cartilage, the composition including HAPLN1 as an active ingredient.

REFERENCE TO SEQUENCE LISTING

Incorporated herein by reference in its entirety is a Sequence Listing in electronic format filed via EFS-Web on May 19, 2020, entitled "0519-000004USNPA_Sequence-Listing.txt," created on Aug. 23, 2018 and being 4,000 bytes in size.

TECHNICAL BACKGROUND

In the hinge part of the human body, where bones meet, articular cartilages composed of hyaline cartilage are in contact with each other to exert an internal pressure and a tensile force, and in each joint, synovial capsule contains synovial fluid to reduce friction during joint motion.

Articular cartilage, together with growth plate cartilage, corresponds to hyaline cartilage among the types of cartilage. An extracellular matrix (ECM) of the cartilage tissues has an aggregate structure of main components such as type II collagen, aggrecan, hyaluronan, and hyaluronan and proteoglycan link protein 1 (HAPLN1), etc. Here, numerous aggrecans bind to a hyaluronan chain, and HAPLN1 is known to play a role in physically and chemically stabilizing aggregates by more strongly binding aggrecans to the hyaluronan chain.

The cartilage thickness in the knee joint is about 2 mm. When an area of about 1 $mm^2$ to about 4 $mm^2$ is damaged by trauma or a disease, regeneration by natural healing is possible. When an area of about 20 $mm^2$ is damaged, self-regeneration is difficult, and generally, great pain is involved. Further, when articular cartilage is completely lost due to various causes such as tumors, necrosis, etc., treatment such as embedding of an artificial joint in the corresponding opening is performed to restore the joint function. However, artificial joints are merely those artificially constructed similarly to joint functions. Since artificial joints are foreign substances in an organism, it is difficult to maintain biocompatibility. In addition, artificial joints are difficult to maintain for more than 20 years because of the complicated operation required under a strict environment of an organism. Deterioration of a resin or metal used as a material thereof, generation of wear debris, or the like may cause a reduction in the function or may cause pain. Further, artificial joints may not be sufficient in durability. Therefore, as a substitute for artificial joint treatment, a technique to regenerate articular cartilage itself has been demanded.

In addition, recent studies have reported regeneration of articular cartilage by perforating the joint surface and placing collagen containing bone morphogenetic protein (BMP) at a desired site. However, the regenerated articular cartilage is not continuously formed with the neighboring existent articular cartilage, and thus it may not be perfect regeneration. Furthermore, application of collagen to an organism is likely to be avoided, due to problems such as bovine spongiform encephalopathy (BSE), so called mad cow disease, etc. Accordingly, there is a need for the development of a new composition for regenerating cartilage using only materials of which biomedical applications are approved.

SUMMARY

An object of the present disclosure is to provide a pharmaceutical composition for regenerating cartilage.

Another object of the present disclosure is to provide a health food composition for regenerating cartilage.

Another object of the present disclosure is to provide a reagent composition for regenerating cartilage.

Still another object of the present disclosure is to provide a method of regenerating cartilage tissues.

To achieve the above objects, the present disclosure provides a pharmaceutical composition for regenerating cartilage, a health food composition for regenerating cartilage, or a reagent composition for regenerating cartilage, each including hyaluronan and proteoglycan link protein 1 (HAPLN1) as an active ingredient.

Further, the present disclosure provides a method of regenerating cartilage tissues by treatment with HAPLN1.

According to the present disclosure, HAPLN1 protein may have cartilage formation-stimulating ability and articular cartilage regeneration ability, and may increase a TGF-β receptor I expression level of chondrocytes to increase a component ratio of cells having cartilage formation ability and to induce generation of cartilage tissues. Accordingly, the HAPLN1 protein of the present disclosure, which is a novel composition for regulating TGF-β signal transduction, may be usefully applied as a pharmaceutical composition for regenerating cartilage, a health food composition for regenerating cartilage, or a reagent composition for regenerating cartilage.

BRIEF DESCRIPTION OF DRAWINGS

FIG. 1A and FIG. 1B show cartilage formation ability by repeated intraperitoneal administration of HAPLN1 protein into degenerated growth plate of old mice, in which

FIG. 3A and FIG. 3B show cartilage formation-stimulating ability of HAPLN1 protein for human articular chondrocytes, in which FIG. 4A, FIG. 4B, FIG. 4C, and FIG. 4D show TGF-β signaling regulation of the HAPLN1 protein for murine articular chondrocytes, in which

DETAILED DESCRIPTION OF EMBODIMENTS

The present inventors of the present disclosure confirmed cartilage formation-stimulating ability and cartilage regeneration ability of hyaluronan and proteoglycan link protein 1 (HAPLN1) protein in old mice and articular cartilage-damaged mice. Further, they confirmed that the cartilage formation-stimulating ability of HAPLN1 protein is effective also in chondrocytes, and also confirmed a signaling regulation effect by increased presentation of TGF-β receptor I of chondrocytes, thereby completing the present disclosure.

The present disclosure provides a pharmaceutical composition for regenerating cartilage, the pharmaceutical composition including HAPLN1 as an active ingredient.

The HAPLN1 may stimulate cartilage formation and may protect articular cartilage.

The HAPLN1 may increase a TGF-β receptor I expression level to increase a component ratio of cells having cartilage formation ability and to induce generation of cartilage tissues.

When the composition of the present disclosure is a pharmaceutical composition, the composition may include, for administration, a pharmaceutically acceptable carrier, excipient, or diluent, in addition to the above-described active ingredient. The carrier, excipient, or diluent may include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methyl hydroxybenzoate, propyl hydroxybenzoate, talc, magnesium stearate, and mineral oil.

The pharmaceutical composition of the present disclosure may be used in the form of an oral formulation such as powder, granules, a tablet, a capsule, a suspension, an emulsion, a syrup, an aerosol, etc., an external preparation, a suppository, or a sterile injectable solution, respectively, according to a common method. In detail, when formulated, the composition may be prepared using a commonly used diluent or excipient such as a filler, an extender, a binder, a wetting agent, a disintegrating agent, a surfactant, etc. Solid formulations for oral administration include tablets, pills, powders, granules, capsules, etc., but are not limited thereto. Such solid formulations may be prepared by mixing one or more excipients, for example, starch, calcium carbonate, sucrose, lactose, gelatin, etc., in addition to the active ingredient. Further, lubricants such as magnesium stearate and talc may also be used, in addition to simple excipients. In addition to a liquid for oral administration or a liquid paraffin, various excipients, for example, a wetting agent, a sweetener, a flavoring agent, a preservative, etc. may be added for preparation. Formulations for parenteral administration include sterile aqueous solutions, non-aqueous solvents, suspensions, emulsions, lyophilized preparations, and suppositories. For non-aqueous solvents and suspensions, propylene glycol, polyethylene glycol, a vegetable oil such as olive oil, and an injectable ester such as ethyl oleate may be used. As bases for suppositories, WITEPSOL, macrogol, TWEEN 61, cacao butter, laurin butter, glycerogelatin, etc. may be used.

An appropriate administration dose of the pharmaceutical composition of the present disclosure may vary depending on a patient's conditions and weight, severity of a disease, a drug form, and time, and may be suitably chosen by those skilled in the art. A daily dose of the composition may be 0.001 mg/kg to 50 mg/kg, and if necessary, administered once a day or in several divided doses a day.

Further, the present disclosure provides a health food composition for regenerating cartilage, the health food composition including HAPLN1 as an active ingredient.

When the composition of the present disclosure is a health food composition, the composition may include a variety of nutrients, vitamins, minerals (electrolytes), a flavoring agent such as synthetic and natural flavoring agents, etc., a colorant and a filler (cheese, chocolate, etc.), pectic acid or salts thereof, alginic acid or salts thereof, an organic acid, a protective colloidal thickening agent, a pH modifier, a stabilizer, a preservative, glycerin, alcohols, a carbonating agent used in carbonated beverages, etc. In addition, the composition may include pulp for preparing natural fruit juices, synthetic fruit juices, and vegetable drinks. These ingredients may be used independently or in combination. In addition, the health food composition may be in any form of meats, sausages, bread, chocolates, candy, snacks, confectionery, pizza, instant noodles, gums, ice cream, soups, beverages, tea, functional water, drinks, alcoholic beverages, and vitamin complexes.

In addition, the health food composition may further include a food additive, and suitability as the food additive is determined based on a scale and a standard for the corresponding item according to the general regulations and general test methods of the Food Additives Codex approved by the Korean Food and Drug Administration unless otherwise provided.

Items disclosed in the Food Additives Codex may include, for example, chemical synthetic products such as ketones, glycine, potassium citrate, nicotinic acid, cinnamic acid, etc.; natural additives such as persimmon color, licorice extract, crystalline cellulose, kaoliang color, guar gums, etc.; and mixed agents such as a sodium L-glutamate agent, a noodles-added alkaline agent, a preservative agent, a tar coloring agent, etc.

In this regard, the composition according to the present disclosure, which is added to foods during the process of preparing the health food composition, may be appropriately added or subtracted, if necessary.

Further, the present disclosure provides a reagent composition for regenerating cartilage, the reagent composition including HAPLN1 as an active ingredient.

Further, the present disclosure provides a method of regenerating cartilage tissues by treatment with HAPLN1.

The HAPLN1 may stimulate cartilage formation and may protect articular cartilage.

The HAPLN1 may increase a TGF-β receptor I expression level to increase a component ratio of cells having cartilage formation ability and to induce generation of cartilage tissues.

Hereinafter, the present disclosure will be described in more detail with reference to exemplary embodiments. These exemplary embodiments are only for illustrating the present disclosure in more detail, and it will be apparent to those skilled in the art that the scope of the present disclosure is not limited to these exemplary embodiments in accordance with the gist of the present disclosure.

EXAMPLE 1

Analysis of Cartilage Regeneration Ability of Hyaluronan and Proteoglycan Link Protein 1 (HAPLN1) Protein In Degenerated Cartilage Tissue In Vivo

1.1 Stimulation of Cartilage Formation In Degenerated Growth Plate By Repeated Intraperitoneal Administration of HAPLN1 Protein 6-week-old male C57BL/6 mice were classified as a young group, and 20-month-old C57BL/6 mice were classified as an old group. The old group was intraperitoneally administered with HAPLN1 protein diluted with phosphate buffered saline (PBS) at a dose of 0.1 mg/kg daily for 2 weeks, whereas the control group was intraperitoneally administered with PBS in an equivalent manner.

The mouse femur and knee joints of each group were taken and fixed with neutral buffered 10% formalin (NBF) for 48 hours, followed by decalcification with a 10% ethylenediaminetetraacetic acid (EDTA) solution for 7 days. Subsequently, each sample was embedded in paraffin to prepare a paraffin block, and a 5 μm-thick tissue section slide was prepared in a sagittal direction. For histological evaluation, the cartilage tissue of each tissue section slide was visualized by safranin O/fast green FCF (SO/FG) staining. The stained tissue sections were observed and photographed using a Ni-U (Nikon) microscope and DS-Ri1 (Nikon) digital camera, and the results are shown in FIG. 1A (scale bar=1 mm).

Figure 1A:
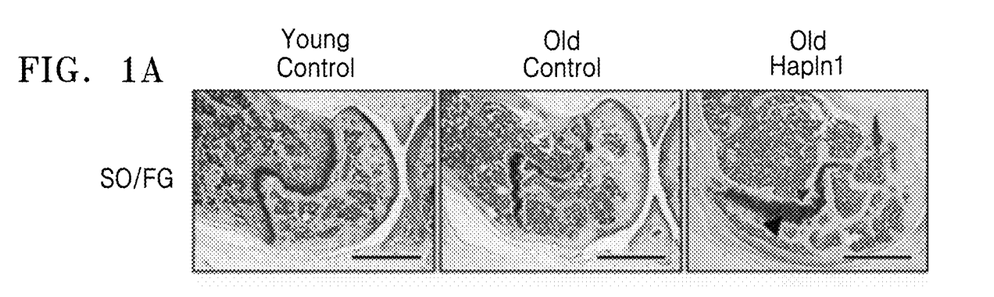
FIG. 1A shows proteoglycan in tissues, as visualized by safranin O/Fast Green FCF staining.

As shown in FIG. 1A, the growth plate of the old control was degenerated and only traces of the cartilage tissue was identified, as compared with that of the young control, while cartilage formation was observed in the degenerated growth plate of the old group (Old HAPLN1), which was repeatedly intraperitoneally administered with HAPLN1 protein (arrow head).

1-2. Formation and Increase of Chondrocytes Having Cartilage Formation Ability By Repeated Intraperitoneal Administration of HAPLN1 Protein To identify the presence of cells having the cartilage formation ability at the site of cartilage formation, which was induced by repeated intraperitoneal administration of HAPLN1 protein in Example 1-1, the corresponding site was stained by immunohistochemistry (IHC) using SOX9, which is a cartilage-specific transcription factor. The stained tissue sections were observed and photographed using a Ni-U (Nikon) microscope and a DS-Ri1 (Nikon) digital camera, and the results are shown in FIG. 1B (scale bar=1 mm).

Figure 1B:
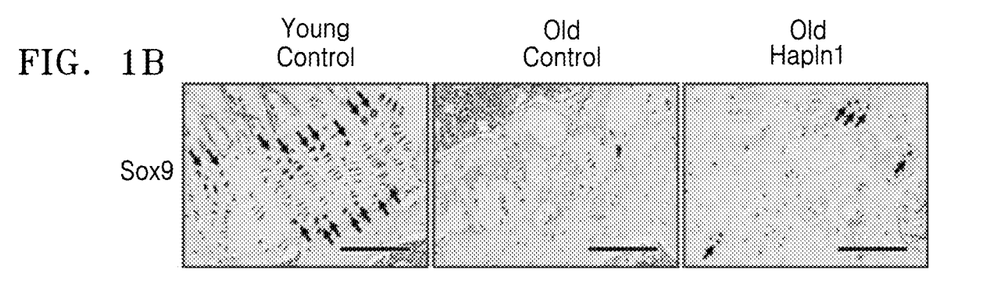
FIG. 1B shows the presence of chondrocytes having cartilage formation ability, as visualized by immunohistochemistry.

As shown in FIG. 1B, SOX9-expressing cells were retained throughout the cartilage tissue in the young control, whereas no SOX9-expressing cells were found in the old control. However, it was confirmed that a large number of SOX9-expressing cells were found in the cartilage formation-stimulated site of the old group (Old HAPLN1), which was repeatedly intraperitoneally administered with HAPLN1 protein (arrow).

EXAMPLE 2

Analysis of Cartilage Regeneration Ability of HAPLN1 Protein In Damaged Cartilage Tissue In Vivo 7-week-old male C57BL/6 mice were divided into three groups as follows. A normal control group (sham control group), which is a sham operation group for a destabilization of medial meniscus (DMM) procedure, was bred under the existing conditions for 4 weeks after the procedure. A vehicle treatment group (DMM control group) was bred under the existing conditions for 8 weeks after the DMM procedure, and intraarticularly administered with PBS once a week for the last 4 weeks. A HAPLN1 treatment group (DMM HAPLN1 group) was bred under the existing conditions for 8 weeks after the DMM procedure, and intraarticularly administered with HAPLN1 protein in PBS at a concentration of 1 μg/mL once a week for the last 4 weeks.

At the end of breeding, each knee tissue to which the procedure and treatment were applied was removed and fixed with NBF for 48 hours, and subsequently decalcified with a 10% EDTA solution for 7 days. Subsequently, each sample was embedded in paraffin to prepare a paraffin block, and a 5 μm thick tissue section slide was prepared in a sagittal direction. Type II collagen (Col2) was stained with green fluorescence by immunofluorescence (IF), and nuclei of cells were blue stained with 4',6-diamidino-2-phenylindole (DAPI). The stained tissue sections were observed and photographed using a Ni-U (Nikon) microscope and a DS-Ri1 (Nikon) digital camera, and the results are shown in FIG. 2 (scale bar=200 μm).

Figure 2:
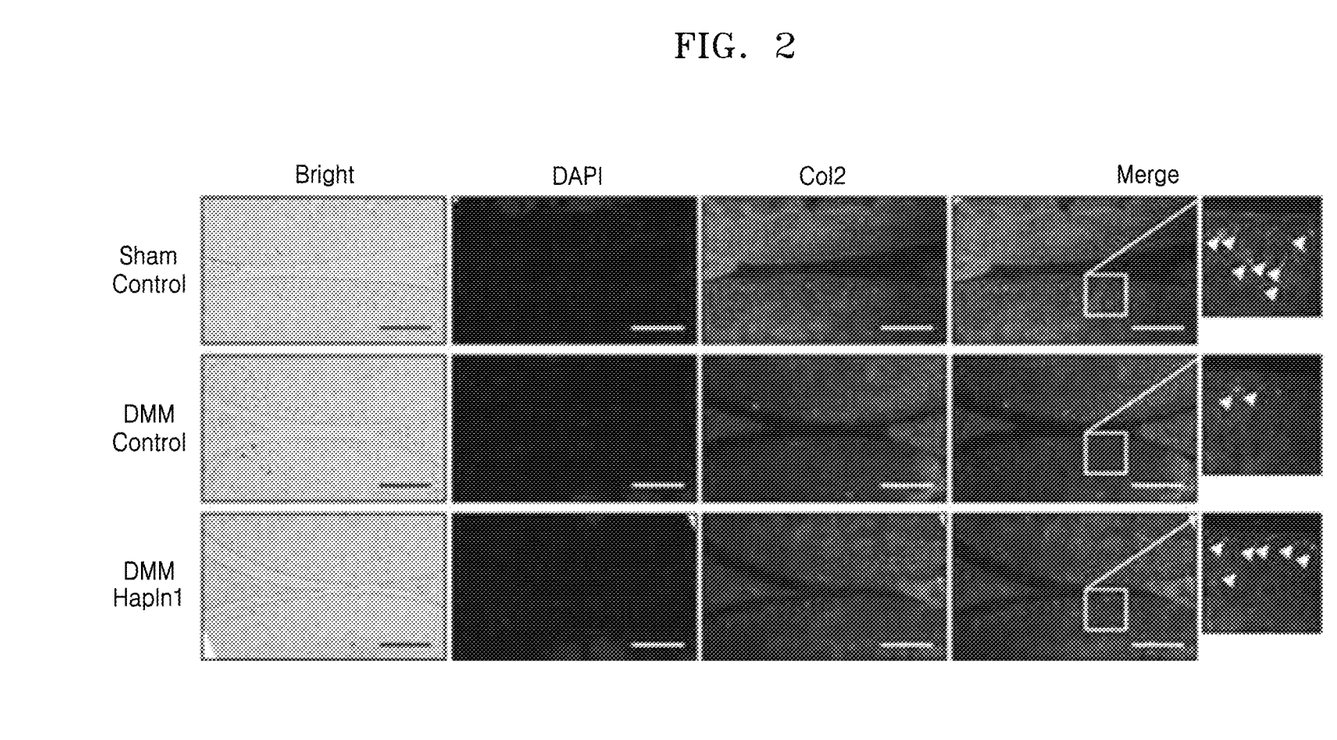
FIG. 2 shows cartilage regeneration ability of HAPLN1 protein intraarticularly administered into damaged knee joint tissues of mice, as visualized by immunofluorescence.

As shown in FIG. 2, it was confirmed that the number of type II collagen-expressing cells found in the normal control group (sham control group) was greatly reduced in the vehicle treatment group (DMM control group), whereas the number of type II collagen-expressing cells was greatly increased in the HAPLN1 treatment group (DMM HAPLN1 group) (arrow head).

EXAMPLE 3

Analysis of Cartilage Formation-Stimulating Ability of HAPLN1 Protein In Vitro

3-1. Increase of Cartilage Formation Ability of Human Articular Chondrocytes By HAPLN1 Protein Human articular chondrocytes (HACs) were cultured in a 1:1 mixed medium of Dulbecco's modified Eagle medium/F12 (DMEM/F12; Gibco) containing 10% fetal bovine serum (FBS; Gibco), 1% penicillin/streptomycin (Gibco), and 1% non-essential amino acids (NEAA; Gibco) under conditions of 37° C. and 5% $CO_2$.

As a model for testing the cartilage formation ability of HAC, a three-dimensional culture system in which cells were embedded in alginate beads was used. HAC was uniformly mixed in a 1.25% alginate solution to include 30,000 cells per bead. They were cultured by adding 50 μg/mL of L-ascorbic acid 2-phosphate, 1% insulin-transferrin-selenium (ITS; Gibco), and 10 ng/mL of TGF-β1 to the culture medium. To the HAPLN1 treatment group, 50 ng/mL of HAPLN1 was further added. Culture was continued under conditions of 37° C. and 5% $CO_2$ for 7 days to 28 days.

At the end of the incubation, to recover the HAC embedded in the alginate beads, the alginate was dissolved in 55 mM EDTA solution, followed by centrifugation at 500×g for 3 minutes. The cells obtained after centrifugation were subjected to RNA extraction and polymerase chain reaction (PCR) to compare and analyze gene expression patterns. Detailed procedures thereof are as follows.

RNA was extracted using a TRIZOL (Thermo Scientific) solution according to the manufacturer's instructions. First-strand cDNA was synthesized from 0.1 μg of the obtained RNA using oligo-dT20 primers and a SUPERSCRIPT III First-Strand Synthesis Supermix (Invitrogen). The obtained cDNA was subjected to PCR using 200 nM of primers for each gene of interest and IQ SYBR Green Supermix (Bio-Rad). Reaction conditions included maintaining a temperature at 95° C. for the first 5 minutes, followed by 45 cycles having 10 seconds at 95° C., 15 seconds at 62° C., and 20 seconds at 72° C. per a cycle. The amplified signal was measured in real-time by CFX CONNECT (Bio-Rad), and an expression level of the gene of interest was calculated as a relative value to each GAPDH expression level. The results are shown in FIG. 3A, and primer sequences used in PCR for each human gene are as follows.

TABLE 1

| | | |
|---|---|---|
| SOX9 | forward | 5'-AGCGAACGCACATCAAGAC-3' |
| | reverse | 5'-CTGTAGGCGATCTGTTGGGG-3' |
| ACAN | forward | 5'-GTGCCTATCAGGACAAGGTCT-3' |
| | reverse | 5'-GATGCCTTTCACCACGACTTC-3' |
| COL2A1 | forward | 5'-TGGACGCCATGAAGGTTTTCT-3' |
| | reverse | 5'-TGGGAGCCAGATTGTCATCTC-3' |
| GAPDH | forward | 5'-CTGGGCTACACTGAGCACC-3' |
| | reverse | 5'-AAGTGGTCGTTGAGGGCAATG-3' |

Figure 3A:
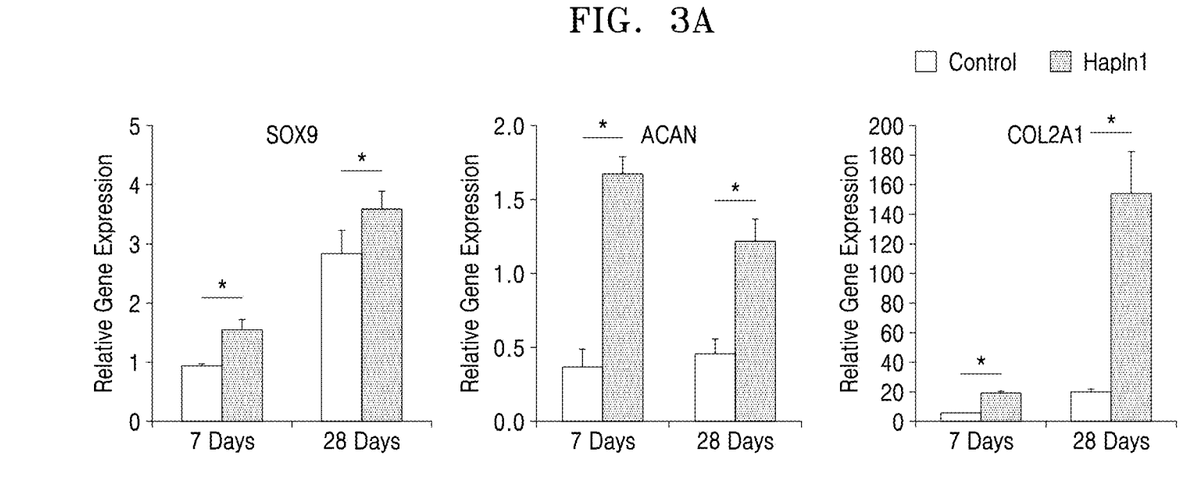
FIG. 3A shows gene expression levels of SOX9 (relative expression, no units), which is a cartilage-specific gene, and aggrecan and type II collagen, which are cartilage matrix components, as determined by a polymerase chain reaction (PCR)

As shown in FIG. 3A, it was confirmed that HAPLN1 protein causes HAC to increase SOX9 gene expression, and at the same time, to increase gene expression of aggrecan (ACAN) and type II collagen (COL2A1).

3-2. Increased Proteoglycan Accumulation In Extracellular Matrix of Human Articular Chondrocyte By HAPLN1 Protein From Example 3-1, to evaluate the extracellular accumulation of the cartilage matrix by HAPLN1 addition, the alginate beads at 28 days of culture were fixed with NBF for 15 minutes and frozen in an OCT compound (Sakura) by liquid nitrogen. Thereafter, 5 μm-thick frozen sections were obtained, and after acetone fixation, visualized by safranin O/Fast Green FCF staining. The stained tissue sections were observed and photographed using a Ni-U (Nikon) microscope and DS-Ri1 (Nikon) digital camera, and the results are shown in FIG. 3B (scale bar=250 μm).

Figure 3B:
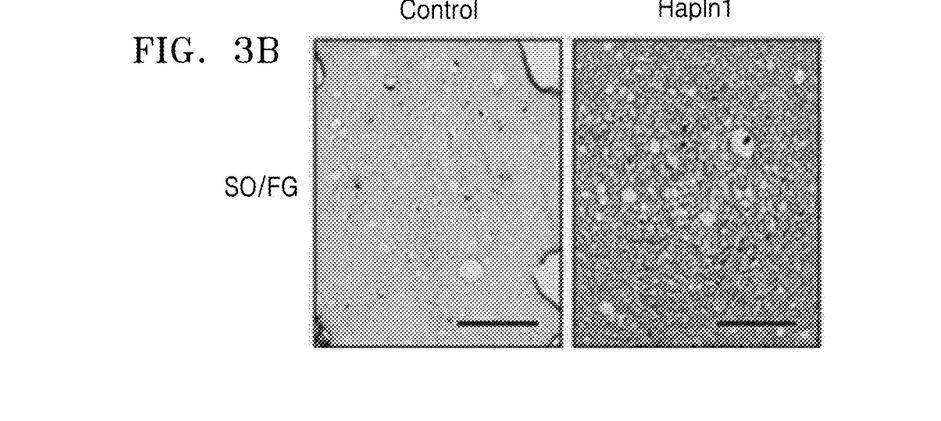
FIG. 3B shows proteoglycan accumulated in extracellular matrix, as visualized by safranin O/Fast Green FCF staining.

As shown in FIG. 3B, it was confirmed that the accumulation of proteoglycans stained with safranin O was greatly increased in the alginate beads of HAC cultured in the medium containing HAPLN1 protein, as compared with the control group.

EXAMPLE 4

Analysis of TGF-β Signaling Regulation by HAPLN1 Protein 4-1. Increased TGF-β Receptor I (TβR1) Protein In Murine Articular Chondrocyte By HAPLN1 Protein Immature murine articular chondrocytes (iMACs) were isolated from bilateral articular cartilage of 5-day-old ICR mice. The obtained iMACs were cultured in a DMEM/F12 (Gibco) medium containing 10% FBS (Gibco), 1% penicillin/streptomycin (Gibco), and
1% NEAA (Gibco) under conditions of 37° C. and 5% $CO_2$.

iMACs cultured at a high density on the plate bottom were treated with 100 ng/mL of HAPLN1 for 3 hours to 72 hours, cells were collected, and proteins were extracted in a radio-immunoprecipitation assay (RIPA) buffer. Next, western blotting was performed to examine expression levels of TGF-β receptor I (TβR1), activin receptor-like kinase 1 (ALK1), TGF-β receptor II (TβR2), and Gapdh proteins, and the results are shown in FIG. 4A.

Figure 4A:
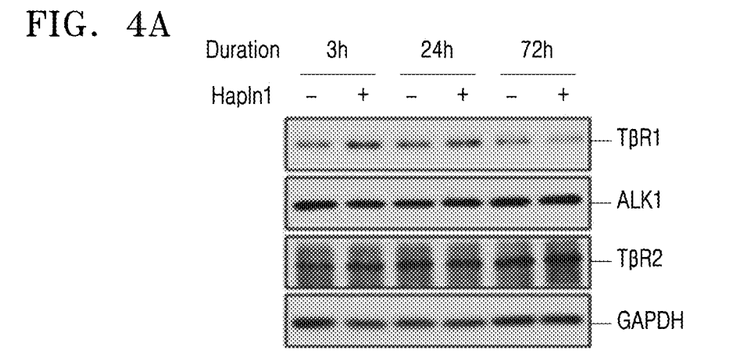
FIG. 4A shows TGF-β receptor I regulation ability of HAPLN1 protein, as examined by western blotting.

As shown in FIG. 4A, it was confirmed that the protein expression level of TβR1 in iMACs was increased by HAPLN1 protein. In contrast, there was no changes in the ALK1 and TβR2 expression levels.

4-2. Increased Stability of TβR1 In Murine Articular Chondrocyte By HAPLN1 Protein To demonstrate that the increased TβR1 protein level by HAPLN1 protein as shown in Example 4-1 was attributed to increased stability, gene expression levels of the three proteins, of which levels were compared, were compared and analyzed in the cells cultured for 24 hours and 72 hours under the same experimental conditions, and at the same time, the increase in the TβR1 protein level by HAPLN1 was demonstrated in de novo protein synthesis-limited environment.

RNA extraction and PCR procedure for the analysis are as follows.

Figure 4B:
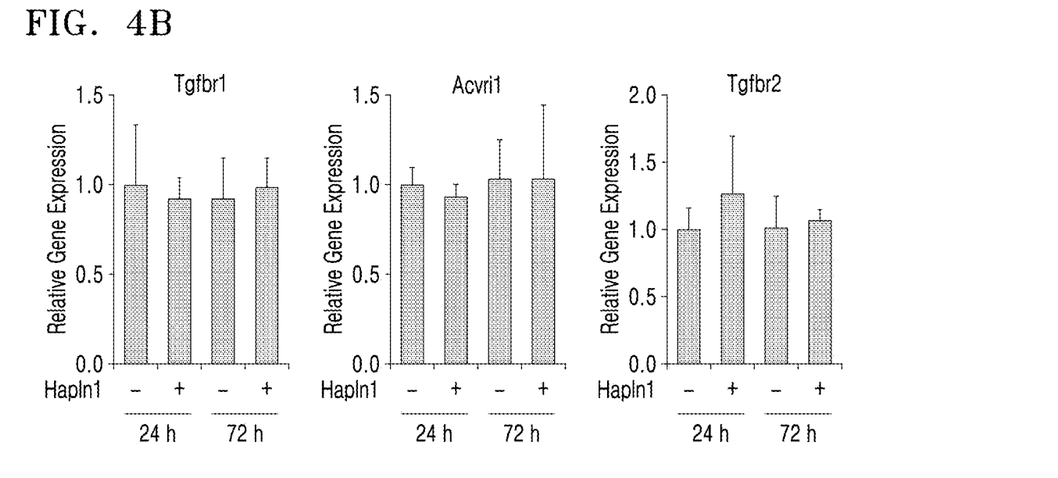
FIGS. 4B and 4C show TGF-β receptor I stabilization of HAPLN1 protein, as examined by a PCR in FIG. 4B (relative expression, no units) and western blotting in FIG. 4C.

RNA was extracted using a TRIZOL (Thermo Scientific) solution according to the manufacturer's instructions. First-strand cDNA was synthesized from 0.1 μg of the obtained RNA using oligo-dT20 primers and a SUPERSCRIPT III First-Strand Synthesis Supermix (Invitrogen). The obtained cDNA was subjected to PCR using 200 nM of primers for each gene of interest and IQ SYBR Green Supermix (Bio-Rad). Reaction conditions included maintaining a temperature at 95° C. for the first 5 minutes, followed by 45 cycles having 10 seconds at 95° C., 15 seconds at 61° C., and 20 seconds at 72° C. per a cycle. The amplified signal was measured in real-time by CFX CONNECT (Bio-Rad), and an expression level of the gene of interest was calculated as a relative value to each GAPDH expression level. The results are shown in FIG. 4B, and primer sequences used in PCR for each mouse gene are as follows.

TABLE 2

| | | |
|---|---|---|
| Tgfbr1 | forward | 5'-GTCACTGGAGTTGTACGGCA-3' |
| | reverse | 5'-GGGCTGATCCCGTTGATTTC-3' |
| Acvrl1 | forward | 5'-CTGGGTGCTCTAGGCTTGTG-3' |
| | reverse | 5'-GCCCGTAGTACAGTCGCTG-3' |
| Tgfbr2 | forward | 5'-AACAGTGATGTCATGGCCAG-3' |
| | reverse | 5'-CAGACTTCATGCGGCTTCTC-3' |
| Gapdh | forward | 5'-TGGCCTTCCGTGTTCCTAC-3' |
| | reverse | 5'-GAGTTGCTGTTGAAGTCGCA-3' |

In addition, 200 ng/mL of HAPLN1 was treated from 0.5 hours (pre) before treatment with cycloheximide (CHX) or from 0.5 hours (post) after treatment with cycloheximide (CHX) while iMACs cultured at a high density on the plate bottom were exposed to 10 μM of cycloheximide (CHX). 24 hours after the CHX treatment, the cell-attached plate was washed with PBS, cells were collected, and proteins were extracted in a RIPA buffer. The extracted cell lysate was subjected to western blotting to examine protein expression levels of TβR1, ALK1, TβR2, and Gapdh, and the results are shown in FIG. 4C.

Figure 4C:
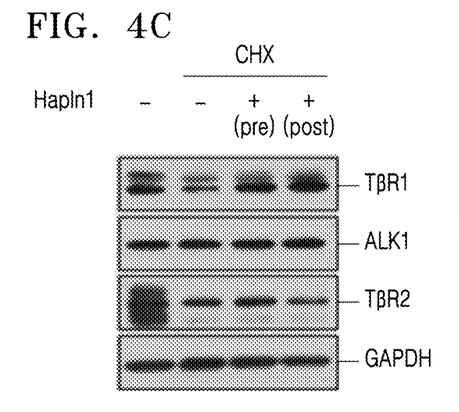

As shown in FIGS. 4B and 4C, none of TβR1, ALK1, and TβR2 gene expressions in iMACs was induced or suppressed by HAPLN1 protein. In addition, it was confirmed that TβR1 showed the increased protein expression level by HAPLN1 protein, unlike ALK1 and TβR2, of which protein expression levels were not changed. This suggests that HAPLN1 protein did not induce transcription of the TβR1 gene but increased its half-life, indicating that the stability of the TβR1 protein possessed by iMACs was increased.

4-3. Increased Cell Surface Presentation of TβR1 In Murine Articular Chondrocytes By HAPLN1 Protein 200 ng/mL of HAPLN1 was treated from 0.5 hours (pre) before treatment with CHX or from 0.5 hours (post) after treatment with CHX while iMACs cultured at a high density on the plate bottom were exposed to 10 μM of CHX. 24 hours after the CHX treatment, the cell-attached plate was washed with PBS and reacted with EZ-Link Sulfo-NHS-LC-Biotin (Thermo Scientific) for 2 hours to label the cell surface protein with biotin. After the reaction was terminated with a 0.1 M glycine solution, cells were collected and proteins were extracted in an NP-40 lysis buffer (Bioworld). Only the biotin-labeled cell surface proteins were selectively extracted from the extracted lysate by immunoprecipitation using a biotin antibody and magnetic beads. A fraction thus obtained was subjected to western blotting to examine the protein expression levels of TβR1, ALK1, TβR2, and Gapdh, and the results are shown in FIG. 4D.

Figure 4D:
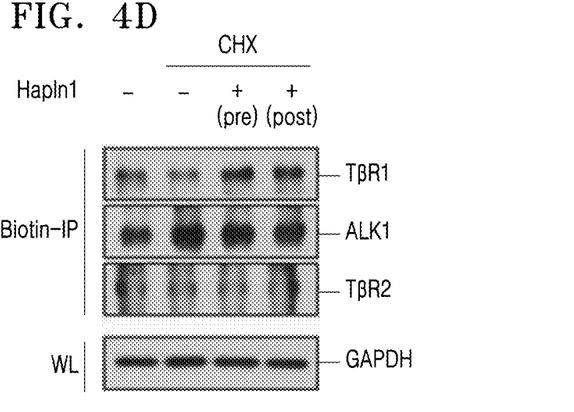
FIG. 4D shows improved cell surface presentation of TGF-β receptor I by HAPLN1 protein, as examined by western blotting.

As shown in FIG. 4D, HAPLN1 protein was found to increase the expression level of TβR1 protein presented on the cell surface of iMACs, and at the same time, there were no changes in the ALK1 and TβR2 expression.

Hereinafter, Preparation Examples of the composition including HAPLN1 according to the present disclosure will be described, and the present disclosure is not limited thereto but for illustrative purpose only.

<Prescription Example 1> Prescription Example of Pharmaceutical Composition

<Prescription Example 1-1> Preparation of Powder Formulation

A powder formulation was prepared by mixing 20 mg of HAPLN1, 100 mg of lactose and 10 mg of talc, and then packing an airtight bag with the mixture.

<Prescription Example 1-2> Preparation of Tablet Formulation

A tablet formulation was prepared by mixing 20 mg of HAPLN1, 100 mg of corn starch, 100 mg of lactose and 2 mg of magnesium stearate, and then tableting the mixture according to a common method of preparing tablets.

<Prescription Example 1-3> Preparation of Capsule Formulation

A capsule formulation was prepared by mixing 10 mg of HAPLN1, 100 mg of corn starch, 100 mg of lactose and 2 mg of magnesium stearate, mixing the components according to a common method of preparing capsules, and packing a gelatin capsule with the mixture.

<Prescription Example 1-4> Preparation of Injectable Formulation 10 mg of HAPLN1, an appropriate amount of injectable sterile distilled water, and an appropriate amount of a pH adjusting agent were mixed, and then prepared in the above-described contents of ingredients per ampoule (2 mL) according to a common method of preparing injectable formulations.

<Prescription Example 1-5> Preparation of Ointment Formulation

An ointment formulation was prepared by mixing 10 mg of HAPLN1, 250 mg of PEG-4000, 650 mg of PEG-400, 10 mg of white vaseline, 1.44 mg of methyl parahydroxybenzoate, 0.18 mg of propyl parahydroxybenzoate, and the remaining amount of purified water according to a common method of preparing ointments.

<Prescription Example 2> Preparation of Health Supplement Food

<Prescription Example 2-1> Preparation of Health Food

Granules were prepared by mixing 1 mg of HAPLN1, an appropriate amount of a vitamin mixture (70 μg of vitamin A acetate, 1.0 mg of vitamin E, 0.13 mg of vitamin B1, 0.15 mg of vitamin B2, 0.5 mg of vitamin B6, 0.2 μg of vitamin B12, 10 mg of vitamin C, 10 μg of biotin, 1.7 mg of nicotinic acid amide, 50 μg of folic acid, and 0.5 mg of calcium pantothenate), and an appropriate amount of a mineral mixture (1.75 mg of ferrous sulfate, 0.82 mg of zinc oxide, 25.3 mg of magnesium carbonate, 15 mg of monopotassium phosphate, 55 mg of calcium phosphate dibasic, 90 mg of potassium citrate, 100 mg of calcium carbonate, and 24.8 mg of magnesium chloride), and a health food was prepared according to a common method.

<Prescription Example 2-2> Preparation of Health Drink 1 mg of HAPLN1, 1000 mg of citric acid, 100 g of oligosaccharide, 2 g of plum concentrate, 1 g of taurine, and purified water were added to a total of 900 mL, and the above ingredients were mixed according to a common method of preparing health drinks, and then heated under stirring at 85° C. for about 1 hr. Then, the resulting solution was filtered and collected in a 2 L sterile container, sealed, sterilized, and then refrigerated.

As described above, although a specific part of the present disclosure has been described in detail, it is apparent to those skilled in the art that the detailed description is only an exemplary embodiment, and is not to be construed to limit the scope of the present disclosure. Therefore, the substantial scope of the present disclosure will be defined by the appended claims and equivalents thereof.

The scope of the present disclosure is represented by the following claims, and it is to be construed that the meaning and scope of the claims and all variations or modified forms derived from the equivalent concept thereof are encompassed within the scope of the present disclosure.

We claim:

1. A method of regenerating cartilage in a subject comprising:
   selecting a subject with degenerated or physically damaged cartilage, and
   administering or applying a therapeutically effective amount of hyaluronan and proteoglycan link protein 1 (HAPLN1) to the subject, thereby regenerating the degenerated or physically damaged cartilage.

2. The method of claim 1, wherein the therapeutically effective amount of HAPLN1 stimulates cartilage formation and protects articular cartilage.

3. The method of claim 1, wherein the therapeutically effective amount of HAPLN1 increases expression of transforming growth factor beta receptor I (TGF-β receptor I) to increase a component ratio of cells having cartilage formation ability.

4. The method of claim 1, wherein the HAPLN1 is administered or applied intraarticularly.

5. The method of claim 1, wherein the therapeutically effective amount of HAPLN1 increases expression of transforming growth factor beta receptor I (TGF-β receptor I) of chondrocytes to increase a component ratio of cells having cartilage formation ability.

6. A method of regenerating cartilage in a subject comprising: selecting a subject with degenerated or physically damaged cartilage, and administering or applying an effective amount of hyaluronan proteoglycan link protein 1 (HAPLN1) as an active ingredient in a health food composition to the subject, thereby regenerating the degenerated or physically damaged cartilage.

* * * * *

SEQUENCE LISTING

<160> NUMBER OF SEQ ID NOS: 16

<210> SEQ ID NO 1
<211> LENGTH: 19
<212> TYPE: DNA
<213> ORGANISM: Artificial Sequence
<220> FEATURE:
<223> OTHER INFORMATION: forward primer for amplifying SOX9

<400> SEQUENCE: 1
agcgaacgca catcaagac                                         19

<210> SEQ ID NO 2
<211> LENGTH: 20
<212> TYPE: DNA
<213> ORGANISM: Artificial Sequence
<220> FEATURE:
<223> OTHER INFORMATION: reverse primer for amplifying SOX9

<400> SEQUENCE: 2
ctgtaggcga tctgttgggg                                        20

<210> SEQ ID NO 3
<211> LENGTH: 21
<212> TYPE: DNA
<213> ORGANISM: Artificial Sequence
<220> FEATURE:
<223> OTHER INFORMATION: forward primer for amplifying ACAN

<400> SEQUENCE: 3
gtgcctatca ggacaaggtc t                                      21

<210> SEQ ID NO 4
<211> LENGTH: 21
<212> TYPE: DNA
<213> ORGANISM: Artificial Sequence
<220> FEATURE:
<223> OTHER INFORMATION: reverse primer for amplifying ACAN

<400> SEQUENCE: 4
gatgcctttc accacgactt c                                      21

<210> SEQ ID NO 5
<211> LENGTH: 21
<212> TYPE: DNA
<213> ORGANISM: Artificial Sequence
<220> FEATURE:
<223> OTHER INFORMATION: forwward primer for amplifying COL2A1

<400> SEQUENCE: 5
tggacgccat gaaggttttc t                                      21

<210> SEQ ID NO 6
<211> LENGTH: 21
<212> TYPE: DNA
<213> ORGANISM: Artificial Sequence
<220> FEATURE:
<223> OTHER INFORMATION: reverse primer for amplifying COL2A1

<400> SEQUENCE: 6
tgggagccag attgtcatct c                                      21

<210> SEQ ID NO 7
<211> LENGTH: 19
<212> TYPE: DNA
<213> ORGANISM: Artificial Sequence

```
<220> FEATURE:
<223> OTHER INFORMATION: forward primer for amplifying GAPDH

<400> SEQUENCE: 7
ctgggctaca ctgagcacc                                                  19

<210> SEQ ID NO 8
<211> LENGTH: 21
<212> TYPE: DNA
<213> ORGANISM: Artificial Sequence
<220> FEATURE:
<223> OTHER INFORMATION: reverse primer for amplifying GAPDH

<400> SEQUENCE: 8
aagtggtcgt tgagggcaat g                                               21

<210> SEQ ID NO 9
<211> LENGTH: 20
<212> TYPE: DNA
<213> ORGANISM: Artificial Sequence
<220> FEATURE:
<223> OTHER INFORMATION: forward primer for amplifying Tgfbr1

<400> SEQUENCE: 9
gtcactggag ttgtacggca                                                 20

<210> SEQ ID NO 10
<211> LENGTH: 20
<212> TYPE: DNA
<213> ORGANISM: Artificial Sequence
<220> FEATURE:
<223> OTHER INFORMATION: reverse primer for amplifying Tgfbr1

<400> SEQUENCE: 10
gggctgatcc cgttgatttc                                                 20

<210> SEQ ID NO 11
<211> LENGTH: 20
<212> TYPE: DNA
<213> ORGANISM: Artificial Sequence
<220> FEATURE:
<223> OTHER INFORMATION: forward primer for amplifying Acvrl1

<400> SEQUENCE: 11
ctgggtgctc taggcttgtg                                                 20

<210> SEQ ID NO 12
<211> LENGTH: 19
<212> TYPE: DNA
<213> ORGANISM: Artificial Sequence
<220> FEATURE:
<223> OTHER INFORMATION: reverse primer for amplifying Acvrl1

<400> SEQUENCE: 12
gcccgtagta cagtcgctg                                                  19

<210> SEQ ID NO 13
<211> LENGTH: 20
<212> TYPE: DNA
<213> ORGANISM: Artificial Sequence
<220> FEATURE:
<223> OTHER INFORMATION: forward primer for amplifying Tgfbr2

<400> SEQUENCE: 13
aacagtgatg tcatggccag                                                 20
```

```
<210> SEQ ID NO 14
<211> LENGTH: 20
<212> TYPE: DNA
<213> ORGANISM: Artificial Sequence
<220> FEATURE:
<223> OTHER INFORMATION: reverse primer for amplifying Tgfbr2

<400> SEQUENCE: 14
cagacttcat gcggcttctc                                                   20

<210> SEQ ID NO 15
<211> LENGTH: 19
<212> TYPE: DNA
<213> ORGANISM: Artificial Sequence
<220> FEATURE:
<223> OTHER INFORMATION: forward primer for amplifying Gapdh

<400> SEQUENCE: 15
tggccttccg tgttcctac                                                    19

<210> SEQ ID NO 16
<211> LENGTH: 20
<212> TYPE: DNA
<213> ORGANISM: Artificial Sequence
<220> FEATURE:
<223> OTHER INFORMATION: reverse primer for amplifying Gapdh

<400> SEQUENCE: 16
gagttgctgt tgaagtcgca                                                   20
```